US010584377B2

(12) United States Patent
Eshoo

(10) Patent No.: US 10,584,377 B2
(45) Date of Patent: *Mar. 10, 2020

(54) DNA SEQUENCING

(71) Applicant: IBIS BIOSCIENCES, INC., Carlsbad, CA (US)

(72) Inventor: Mark W. Eshoo, San Diego, CA (US)

(73) Assignee: IBIS BIOSCIENCES, INC., Carlsbad, CA (US)

(*) Notice: Subject to any disclaimer, the term of this patent is extended or adjusted under 35 U.S.C. 154(b) by 257 days.

This patent is subject to a terminal disclaimer.

(21) Appl. No.: 14/398,271

(22) PCT Filed: May 2, 2013

(86) PCT No.: PCT/US2013/039297
§ 371 (c)(1),
(2) Date: Oct. 31, 2014

(87) PCT Pub. No.: WO2013/166304
PCT Pub. Date: Nov. 7, 2013

(65) Prior Publication Data
US 2015/0111762 A1 Apr. 23, 2015

Related U.S. Application Data

(60) Provisional application No. 61/641,718, filed on May 2, 2012.

(51) Int. Cl.
C12Q 1/68 (2018.01)
C12Q 1/6869 (2018.01)
G16B 30/00 (2019.01)
C12Q 1/6844 (2018.01)

(52) U.S. Cl.
CPC ......... C12Q 1/6869 (2013.01); C12Q 1/6844 (2013.01); G16B 30/00 (2019.02)

(58) Field of Classification Search
None
See application file for complete search history.

(56) References Cited

U.S. PATENT DOCUMENTS

| | | | |
|---|---|---|---|
| 3,996,345 A | 12/1976 | Ullman et al. | |
| 4,351,760 A | 9/1982 | Khanna et al. | |
| 4,415,732 A | 11/1983 | Caruthers et al. | |
| 4,458,066 A | 7/1984 | Caruthers et al. | |
| 4,683,195 A | 7/1987 | Mullis et al. | |
| 4,683,202 A | 7/1987 | Mullis | |
| 4,725,677 A | 2/1988 | Koester et al. | |
| 4,739,044 A | 4/1988 | Stabinsky | |
| 4,757,141 A | 7/1988 | Fung et al. | |
| 4,889,818 A | 12/1989 | Gelfand et al. | |
| 4,973,679 A | 11/1990 | Caruthers et al. | |
| 4,980,460 A | 12/1990 | Molko et al. | |
| 5,695,934 A | 12/1997 | Brenner | |
| 5,714,330 A | 2/1998 | Brenner et al. | |
| 5,750,341 A | 5/1998 | Macevicz | |
| 6,306,597 B1 | 10/2001 | Macevicz | |
| 6,329,178 B1 | 12/2001 | Patel et al. | |
| 6,395,524 B2 | 5/2002 | Loeb et al. | |
| 6,397,150 B1* | 5/2002 | Izmailov | C12Q 1/6869 435/6.12 |
| 6,432,360 B1 | 8/2002 | Church | |
| 6,485,944 B1 | 11/2002 | Church et al. | |
| 6,511,803 B1 | 1/2003 | Church et al. | |
| 6,602,695 B2 | 8/2003 | Patel et al. | |
| 6,787,308 B2 | 9/2004 | Balasubramanian et al. | |
| 6,833,246 B2 | 12/2004 | Balasubramanian | |
| 6,969,488 B2 | 11/2005 | Bridgham et al. | |
| 7,115,400 B1 | 10/2006 | Adessi et al. | |
| 7,170,050 B2 | 1/2007 | Turner et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,405,281 B2 | 7/2008 | Xu et al. | |
| 7,932,034 B2 | 4/2011 | Esfandyarpour et al. | |
| 9,279,154 B2* | 3/2016 | Previte | C12Q 1/6874 |
| 2003/0064366 A1 | 4/2003 | Hardin et al. | |
| 2003/0194740 A1 | 10/2003 | Williams et al. | |
| 2006/0051807 A1 | 3/2006 | Fuller | |
| 2007/0036511 A1 | 2/2007 | Lundquist et al. | |
| 2007/0048748 A1 | 3/2007 | Williams et al. | |
| 2007/0072196 A1 | 3/2007 | Xu et al. | |
| 2007/0077564 A1 | 4/2007 | Roitman et al. | |
| 2007/0128133 A1 | 6/2007 | Eid et al. | |
| 2007/0134128 A1 | 6/2007 | Korlach | |
| 2007/0141598 A1 | 6/2007 | Turner et al. | |

(Continued)

FOREIGN PATENT DOCUMENTS

EP 0320308 B1 11/1993
WO WO-8909283 A1 10/1989

(Continued)

OTHER PUBLICATIONS

Prober et al, Science 238:336-341, 1987.*
Maxam and Gilbert, PNAS 74(2):560-564, 1977.*
Blazej, RG., et al. (2003) Polymorphism ratio sequencing: A new approach for single nucleotide polymorphism discovery and genotyping. Genome Reasearch, vol. 13, p. 287-293.*
Examination report dated Nov. 17, 2016 for European Application No. 13785146 filed May 2, 2013.
Adessi C., et al., "Solid Phase DNA Amplification: Characterisation of Primer Attachment and Amplification Mechanisms," Nucleic Acids Research, 2000, vol. 28 (20), pp. E87.
Agrawal S., et al., "Site-Specific Functionalization of Oligodeoxynucleotides for Non-Radioactive Labelling," Tetrahedron Letters, 1990, vol. 31 (11), pp. 1543-1546.

(Continued)

Primary Examiner — Suryaprabha Chunduru
(74) Attorney, Agent, or Firm — Casimir Jones, S.C.; Kirk Hogan

(57) ABSTRACT

Provided herein is technology relating to sequencing nucleic acids and particularly, but not exclusively, to methods, compositions, and systems for sequencing a nucleic acid using one or more labels and signal amplitude to distinguish bases.

7 Claims, No Drawings

(56) References Cited

U.S. PATENT DOCUMENTS

| | | |
|---|---|---|
| 2007/0161017 A1 | 7/2007 | Eid et al. |
| 2007/0166705 A1 | 7/2007 | Milton et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0009007 A1 | 1/2008 | Lyle et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2010/0028877 A1* | 2/2010 | Schatz ............ C12Q 1/6827 435/6.12 |
| 2010/0074492 A1* | 3/2010 | Shi ............... G01N 27/44717 382/129 |
| 2012/0046177 A1 | 2/2012 | Huang et al. |

FOREIGN PATENT DOCUMENTS

| | | |
|---|---|---|
| WO | WO-9319205 A1 | 9/1993 |
| WO | WO-9323564 A1 | 11/1993 |
| WO | WO-0018957 A1 | 4/2000 |
| WO | WO-0179536 A1 | 10/2001 |
| WO | WO-03087302 A2 | 10/2003 |
| WO | WO-2004018497 A2 | 3/2004 |
| WO | WO-2005123957 A2 | 12/2005 |
| WO | WO-2006084132 A2 | 8/2006 |
| WO | WO-2010075188 A2 | 7/2010 |
| WO | WO 10/117804 * | 10/2010 |
| WO | WO-2010117804 A2 | 10/2010 |
| WO | WO-2011038241 A1 | 3/2011 |

OTHER PUBLICATIONS

Beaucage S.L., et al., "Advances in the Synthesis of Oligonucleotides by the Phosphoramidite Approach," Tetrahedron, 1992, vol. 48 (12), pp. 2223-2311.

Bennett S.T., et al., "Toward the 1,000 Dollars Human Genome," Pharmacogenomics, 2005, vol. 6 (4), pp. 373-382.

Bentley D.R., et al., "Accurate Whole Human Genome Sequencing Using Reversible Terminator Chemistry," Nature, 2008, vol. 456 (7218), pp. 53-59.

Berlman, "Handbook of Fluorescence Spectra of Aromatic Molecules," 2nd edition, Academic Press, New York, 1971.

Birren B., et al., Genome Analysis: vol. 1, Analyzing DNA, Cold Spring Harbor Laboratory Press, N.Y., 1997, 12 Pages, Table of Contents.

Bishop, Ed., "Indicators," Pergamon Press, Oxford, 1972, 2 Pages, Table of Contents.

Braslavsky I., et al., "Sequence Information can be Obtained from Single DNA Molecules," Proceedings of the National Academy of Sciences, 2003, vol. 100 (7), pp. 3960-3964.

Brenner S., et al., "Gene Expression Analysis by Massively Parallel Signature Sequencing (MPSS) on Microbead Arrays," Nature Biotechnology, 2000, vol. 18 (6), pp. 630-634.

Eckstein F., Oligonucleotides and Analogues, IRL Press, 1991, Table of Contents.

Fuller C.W., et al., "The Challenges of Sequencing by Synthesis," Nature Biotechnology, 2009, vol. 27 (11), pp. 1013-1023.

Griffiths, Colour and Constitution of Organic Molecules, Academic Press, New York, 1976.

Guo J., et al., "Four-Color DNA Sequencing With 3'-O-Modified Nucleotide Reversible Terminators and Chemically Cleavable Fluorescent Dideoxynucleotides," Proceedings of theNational Academyof Sciences, 2008, vol. 105 (27), pp. 9145-9150.

Gyllensten U.B., et al., "Generation of Single-Stranded DNA by the Polymerase Chain Reaction and its Application to Direct Sequencing of the Hla-Dqa Locus," Proceedings of the National Academy of Sciences of the United States of America, 1988, vol. 85 (20), pp. 7652-7656.

Harris T.D., et al., "Single-molecule Dna Sequencing of a Viral Genome," Science, 2008, vol. 320 (5872), pp. 106-109.

Haugland, Handbook of Fluorescent Probes and Research Chemicals, Molecular Probes, Eugene, 1992.

Hyman E.D., "A New Method of Sequencing DNA," Analytical Biochemistry, 1988, vol. 174 (2), pp. 423-436.

Innis M.A., et al., PCR Protocols—A Guide to Methods and Applications, Academic Press Inc., 1990, Table of Contents.

International Search Report and Written Opinion for Application No. PCT/US2013/39297, dated Sep. 18, 2013, 11 pages.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

Kricka et al., "Molecular Probing, Blotting, and Sequencing," especially Chapter 1 Labels, Labeling, Analytical Strategies, and Applications and Table IX, Academic Press, New York, 1995.

Li J.G., et al., "Tag/Anti-Tag Liquid-Phase Primer Extension Array: a Flexible and Versatile Genotyping Platform," Genomics, 2006, vol. 87 (1), pp. 151-157.

Loh E.Y., et al., "Polymerase Chain Reaction With Single-Sided Specificity: Analysis of T Cell Receptor Delta Chain," Science (New York, N.Y.), 1989, vol. 243 (4888), pp. 217-220.

MacLean D., et al., "Application of 'next-generation' Sequencing Technologies to Microbial Genetics," Nature Reviews Microbiology, 2009, vol. 7 (4), pp. 287-296.

Mardis E.R., "Next-Generation DNA Sequencing Methods," Annual Review of Genomics and Human Genetics, 2008, vol. 9, pp. 387-402.

Margulies M., et al., "Genome Sequencing in Microfabricated High-Density Picolitre Reactors," Nature, 2005, vol. 437 (7057), pp. 376-380.

Metzker M.L., "Emerging Technologies in DNA Sequencing," Genome Research, 2005, vol. 15 (12), pp. 1767-1776.

Mitra R.D., et al., "Fluorescent in Situ Sequencing on Polymerase Colonies," Analytical Biochemistry, 2003, vol. 320 (1), pp. 55-65.

Morozova O., et al., "Applications of Next-generation Sequencing Technologies in Functional Genomics," Genomics, 2008, vol. 92 (5), pp. 255-264.

Moyer P., et al., "Near-Field Optical Microscopes Break the Diffraction Limit," Laser Focus World, 1993, vol. 29, 6 pages.

Nelson P.S., et al., "Bifunctional Oligonucleotide Probes Synthesized Using a Novel CPG Support are able to Detect Single Base Pair Mutations," Nucleic Acids Research, 1989, vol. 17 (18), pp. 7187-7194.

Ochman H., et al., "Genetic Applications of an Inverse Polymerase Chain Reaction," Genetics, 1988, vol. 120 (3), pp. 621-623.

Pringsheim, Fluorescence and Phosphorescence, Interscience Publishers, New York, 1949.

Ronaghi M., et al., "A sequencing method based on real-time pyrophosphate," Science, 1998, vol. 281 (5375), pp. 363-365.

(56) References Cited

OTHER PUBLICATIONS

Sambrook J., et al., eds., Molecular Cloning: A Laboratory Manual, 3rd Edition, Cold Spring Harbor Laboratory, 2001, Table of Contents.

Seo T.S., et al., "Four-color DNA Sequencing by Synthesis on a Chip Using Photocleavable Fluorescent Nucleotides," Proceedings of the National Academy of Sciences of the United States of America, 2005, vol. 102 (17), pp. 5926-5931.

Sharma P., et al., "A General Method for the Synthesis of 3'-Sulfhydryl and Phosphate Group Containing Oligonucleotides," Nucleic Acids Research, 1991, vol. 19 (11), pp. 3019-3025.

Shendure J., et al., "Accurate Multiplex Polony Sequencing of an Evolved Bacterial Genome," Science, 2005, vol. 309 (5741), pp. 1728-1732.

Sproat B.S., et al., "The Synthesis of Protected 5'-Mercapto-2',5'-Dideoxyribonucleoside-3'-0-Phosphorainidites; Uses of 5'-Mercapto-Oligodeoxyribonucleotides," Nucleic Acids Research, 1987, vol. 15 (12), pp. 4837-4848.

Stickland J.E., et al., "Quantification of Oncogene Dosage in Tumours by Simultaneous Dual-Label Hybridization," Oncogene, 1993, vol. 8 (1), pp. 223-227.

Supplementary European Search Report for Application No. EP13785146, dated Dec. 18, 2015, 11 pages.

Turcatti G., et al., "A New Class of Cleavable Fluorescent Nucleotides: Synthesis and Optimization as Reversible Terminators for DNA Sequencing by Synthesis," Nucleic Acids Research, 2008, vol. 36 (4), pp. e25.

Voelkerding K.V., et al., "Next-Generation Sequencing: from Basic Research to Diagnostics," Clinical Chemistry, 2009, vol. 55 (4), pp. 641-658.

Wu W., et al., "Termination of DNA Synthesis by N6-Alkylated, Not 3'-O-Alkylated, Photocleavable 2'-Deoxyadenosine Triphosphates," Nucleic Acids Research, 2007, vol. 35 (19), pp. 6339-6349.

Zuckermann R., et al., "Efficient Methods for Attachment of Thiol Specific Probes to the 3'-Ends of Synthetic Oligodeoxyribonucleotides," Nucleic Acids Research, 1987, vol. 15 (13), pp. 5305-5321.

* cited by examiner

DNA SEQUENCING

CROSS-REFERENCE TO RELATED APPLICATIONS

The present Application claims priority to U.S. Provisional Application Ser. No. 61/641,718 filed 2 May 2012, the entirety of which is incorporated by reference herein.

FIELD OF INVENTION

Provided herein is technology relating to sequencing nucleic acids and particularly, but not exclusively, to methods, compositions, and systems for sequencing a nucleic acid using one or more labels and signal amplitude to distinguish bases.

BACKGROUND

DNA sequencing is driving genomics research and discovery. The completion of the Human Genome Project was a monumental achievement with incredible amount of combined efforts among genome centers and scientists worldwide. This decade-long project was completed using the Sanger sequencing method, which remains the staple genome sequencing methodology in high-throughput genome sequencing centers. The main reason behind the prolonged success of this method is its basic and efficient, yet elegant, method of dideoxy chain termination. With incremental improvements in Sanger sequencing—including the use of laser-induced fluorescent excitation of energy transfer dyes, engineered DNA polymerases, capillary electrophoresis, sample preparation, informatics, and sequence analysis software—the Sanger sequencing platform has been able to maintain its status. Current state-of-the-art Sanger based DNA sequencers can produce over 700 bases of clearly readable sequence in a single run from templates up to 30 kb in length. However, as it is with most technological inventions, the continual improvements in this sequencing platform has come to a stagnant plateau, with the current cost estimate for producing a high-quality microbial genome draft sequence at around $10,000 per megabase pair. Current DNA sequencers based on the Sanger method allow up to 384 samples to be analyzed in parallel.

It is evident that exploiting the complete human genome sequence for clinical medicine and health care requires accurate low-cost and high-throughput DNA sequencing methods. Indeed, both public (National Human Genome Research Institute, NHGRI) and private genomic sciences sector (The J. Craig Venter Science Foundation and Archon X prize for genomics) have issued a call for the development of next-generation sequencing technology that will reduce the cost of sequencing to one-ten thousandth of its current cost over the next ten years. Accordingly, to overcome the limitations of current conventional sequencing technologies, a variety of new DNA sequencing methods have been investigated, including sequencing-by-synthesis (SBS) approaches such as pyrosequencing (Ronaghi et al. (1998) *Science* 281: 363-365), sequencing of single DNA molecules (Braslaysky et al. (2003) *Proc. Natl. Acad. Sci. USA* 100: 3960-3964), and polymerase colonies ("polony" sequencing) (Mitra et al. (2003) *Anal. Biochem.* 320: 55-65).

The concept of DNA sequencing-by-synthesis (SBS) was revealed in 1988 with an attempt to sequence DNA by detecting the pyrophosphate group that is generated when a nucleotide is incorporated by a DNA polymerase reaction (Hyman (1999) *Anal. Biochem.* 174: 423-436). Subsequent SBS technologies were based on additional ways to detect the incorporation of a nucleotide to a growing DNA strand. In general, conventional SBS uses an oligonucleotide primer designed to anneal to a predetermined position of the sample template molecule to be sequenced. The primer-template complex is presented with a nucleotide in the presence of a polymerase enzyme. If the nucleotide is complementary to the position on the sample template molecule that is directly 3' of the end of the oligonucleotide primer, then the DNA polymerase will extend the primer with the nucleotide. The incorporation of the nucleotide and the identity of the inserted nucleotide can then be detected by, e.g., the emission of light, a change in fluorescence, a change in pH (see, e.g., U.S. Pat. No. 7,932,034), a change in enzyme conformation, or some other physical or chemical change in the reaction (see, e.g., WO 1993/023564 and WO 1989/009283; Seo et al. (2005) "Four-color DNA sequencing by synthesis on a chip using photocleavable fluorescent nucleotides," *PNAS* 102: 5926-59). Upon each successful incorporation of a nucleotide, a signal is detected that reflects the occurrence, identity, and number of nucleotide incorporations. Unincorporated nucleotides can then be removed (e.g., by chemical degradation or by washing) and the next position in the primer-template can be queried with another nucleotide species.

SUMMARY

In conventional DNA sequencing-by-synthesis using labeled nucleotide monomers, four different moieties (e.g., a dye or a fluorescent label) are attached to the four nucleotide bases to allow the detector to distinguish the bases from each other. For example, some methods label each of the A, C, G, and T with a fluorescent moiety that emits light at a wavelength that is distinguishable from the light emitted by the other three fluorescent moieties, e.g., to produce light of four different colors associated with each of the four bases.

In contrast, the present technology is based on detecting differences in signal amplitude rather than differences in signal wavelength (e.g., color) to identify each base incorporated during a sequencing reaction. In this scheme, each individual base is labeled with the same moiety (e.g., a dye, a fluorescent label, etc.) at a different known percentage (e.g., a "label fraction" or "extent of labeling"). As an exemplary embodiment, 25% of the ATP molecules are labeled, 50% of the TTP molecules are labeled, 75% of the GTP molecules are labeled, and 100% of the CTP molecules are labeled. Then, according to some embodiments, an ensemble (e.g., a polony or a clonal colony) based sequencing approach is performed and the sequence is determined by detecting a signal intensity after each base incorporation and associating the intensities with the bases.

In some embodiments, an element of the technology that allows separating and assigning the signal intensities into appropriate base-specific "bins" is the use of a 4-base calibration sequence at the beginning of a sequencing run. This calibration sequence contains each of the 4 bases in a known order to provide a calibration reference, e.g., to calibrate a sequencing instrument to recognize the appropriate signal intensities for each of the bases.

As a consequence, embodiments of the technology reduce the number of fluorescent dyes needed to identify the four bases (e.g., allowing one to use only the most optimal dye or dyes to acquire a sequence), reduce the number of lasers used to excite the fluorescent moiety or moieties, reduce or eliminate optics used to split the optical signal by wavelength, and reduce of the number of detectors for recording incorporation events.

Accordingly, provided herein is technology related to a method for sequencing a target nucleic acid, the method comprising detecting an amplitude of a signal produced from a plurality of a nucleotide base; and associating the amplitude with the nucleotide base to identify the nucleotide base. In some embodiments, the amplitude of the signal produced by the plurality of the nucleotide base is detectably different than a second amplitude of a second signal produced by a second plurality of a second nucleotide base. For instance, in some embodiments, a fraction of the plurality of the nucleotide base produces a signal, e.g., in some embodiments the plurality of the nucleotide base is detectably labeled.

In one aspect, the technology relates to identifying the nucleotide bases in a nucleotide sequence by a sequencing reaction. Thus, the technology provides in some embodiments a method for sequencing a nucleic acid wherein a fraction of the plurality of the nucleotide base is detectably labeled and said fraction is different than a second fraction of a second plurality of a second nucleotide base that is detectably labeled. Some embodiments of the methods comprise providing a first plurality of a first nucleotide base and a second plurality of a second nucleotide base, wherein a first fraction of the first plurality of the first base is labeled with a label and a second fraction of the second plurality of the second nucleotide base is labeled with said label.

In some embodiments, the methods comprise providing a first plurality of a first nucleotide base, a second plurality of a second nucleotide base, a third plurality of a third nucleotide base, and a fourth plurality of a fourth nucleotide base, wherein a first fraction of the first plurality of the first base is labeled with a label, a second fraction of the second plurality of the second nucleotide base is labeled with said label, a third fraction of the third plurality of the third nucleotide base is labeled with said label, and a fourth fraction of the fourth plurality of the fourth nucleotide base is labeled with said label. For example, in some embodiments, the first nucleotide base is A, the second nucleotide base is C, the third nucleotide base is G, and the fourth nucleotide base is T. Moreover, in some embodiments the label is a fluorescent moiety.

Alternative schemes for identifying nucleotide bases are provided herein. For example, the technology includes a method comprising providing a first plurality of a first nucleotide base, a second plurality of a second nucleotide base, a third plurality of a third nucleotide base, and a fourth plurality of a fourth nucleotide base, wherein a first fraction of the first plurality of the first base is labeled with a first label, a second fraction of the second plurality of the second nucleotide base is labeled with the first label, a third fraction of the third plurality of the third nucleotide base is labeled with a second label, and a fourth fraction of the fourth plurality of the fourth nucleotide base is labeled with the second label.

The methods provided herein relate in some aspects to sequencing a nucleic acid using a sequencing-by-synthesis method. For example, some embodiments provide a method comprising incorporating by polymerization the plurality of the nucleotide base into a plurality of a nucleic acid that is complementary to the target nucleic acid.

In some embodiments, the signal is an electromagnetic wave, e.g., a signal having a wavelength in the visible range. For instance, in some embodiments, the signal is fluorescence. And, moreover, in some embodiments, the methods provide for detecting the signal with an optical device.

Nucleotides of a nucleic acid sequence are identified by monitoring the amplitude of the signal produced during sequencing. Associations between a signal amplitude and the identity or type of a nucleotide base are defined in some embodiments by calibrating a sequencing apparatus with a calibration sequence comprising a known order of nucleotide bases. Accordingly, the technology relates to a method comprising providing a calibration oligonucleotide comprising a known sequence. In addition, the methods provided relate to determining the nucleotide sequence of a nucleic acid; thus, some embodiments of methods further comprise analyzing a dataset of ordered amplitudes to produce a nucleotide sequence of the target nucleic acid.

Another aspect of the technology provides a composition comprising a plurality of a nucleotide base wherein a fraction of the plurality is detectably labeled with a label. Such a composition finds use, for example, in methods for sequencing a nucleic acid. In some embodiments, the compositions provided herein further comprise a second plurality of a second nucleotide base wherein a second fraction of the second plurality is detectably labeled with said label. Moreover, in yet additional embodiments, compositions are provided that comprise a third plurality of a third nucleotide base and a fourth plurality of a fourth nucleotide base, wherein a third fraction of the third plurality of the third nucleotide base is labeled with said label and a fourth fraction of the fourth plurality of the fourth nucleotide base is labeled with said label. In some embodiments, the first nucleotide base is A, the second nucleotide base is C, the third nucleotide base is G, and the fourth nucleotide base is T (or, as appropriate, U) and, in addition, some embodiments provide that the label is a fluorescent moiety. In some embodiments, the first, the second, the third, and/or the fourth base is a modified base or a base analogue such as an inosine, isoguanine, isocytosine, a diaminopyrimidine, a xanthine, a nitroazole, a size-expanded base, etc.

In alternative labeling schemes, embodiments provide compositions further comprising a second plurality of a second nucleotide base wherein a second fraction of the second plurality is detectably labeled with a second label or compositions further comprising a third plurality of a third nucleotide base and a fourth plurality of a fourth nucleotide base, wherein a third fraction of the third plurality of the third nucleotide base is labeled with said label and a fourth fraction of the fourth plurality of the fourth nucleotide base is labeled with said second label.

While the technology relates to compositions of labeled nucleotides, it is to be understood that the technology also includes compositions further comprising a target nucleic acid, a sequencing primer, and a polymerase and/or compositions further comprising a nucleic acid comprising the nucleotide base.

The technology is embodied in systems that incorporate features of the methods and compositions provided. For example, particular embodiments provide a system for sequencing a nucleic acid, wherein the system comprises a composition comprising a plurality of a nucleotide base wherein a fraction of the plurality is detectably labeled with a label; and a calibration oligonucleotide. Some embodiments further comprise a sequencing apparatus, some embodiments further comprise a processor configured to associate an amplitude of a signal with a nucleotide base, and some embodiments further comprise an output functionality to provide a nucleotide sequence of the nucleic acid.

In particular embodiments, systems are provided that further comprise a second plurality of a second nucleotide base, a third plurality of a third nucleotide base, and a fourth plurality of a fourth nucleotide base, wherein a second fraction of the second plurality of the second nucleotide base is labeled with said label, a third fraction of the third plurality of the third nucleotide base is labeled with said label, and a fourth fraction of the fourth plurality of the fourth nucleotide base is labeled with said label. Furthermore, some embodiments comprise a functionality to detect the label and/or a functionality to differentiate the nucleotide base, the second nucleotide base, the third nucleotide base, and the fourth nucleotide base from one another.

Embodiments of kits for nucleic acid sequencing are provided. For example, some embodiments of the technology are kits for sequencing a nucleic acid, wherein the kits comprise a composition comprising a plurality of a nucleotide base wherein a fraction of the plurality is detectably labeled with a label; and a calibration oligonucleotide. Additional embodiments further comprise a second plurality of a second nucleotide base, a third plurality of a third nucleotide base, and a fourth plurality of a fourth nucleotide base, wherein a second fraction of the second plurality of the second nucleotide base is labeled with said label, a third fraction of the third plurality of the third nucleotide base is labeled with said label, and a fourth fraction of the fourth plurality of the fourth nucleotide base is labeled with said label.

Additional embodiments will be apparent to persons skilled in the relevant art based on the teachings contained herein.

DETAILED DESCRIPTION

Provided herein is technology relating to sequencing nucleic acids and particularly, but not exclusively, to methods, compositions, systems, and kits for sequencing a nucleic acid using one or more labels and signal amplitude to distinguish bases.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligonucleotide or polynucleotide chemistry and hybridization described herein are those well known and commonly used in the art. Unless otherwise indicated, standard techniques are used, for example, for nucleic acid purification and preparation, chemical analysis, recombinant nucleic acid, and oligonucleotide synthesis. Enzymatic reactions and purification techniques are performed according to manufacturers' specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. (2000)). The nomenclatures utilized in connection with, and the laboratory procedures and techniques described herein are those well known and commonly used in the art.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

A "system" denotes a set of components, real or abstract, comprising a whole where each component interacts with or is related to at least one other component within the whole.

As used herein, the phrase "dNTP" means deoxynucleotidetriphosphate, where the nucleotide comprises a nucleotide base, such as A, T, C, G or U.

The term "monomer" as used herein means any compound that can be incorporated into a growing molecular chain by a given polymerase. Such monomers include, without limitations, naturally occurring nucleotides (e.g., ATP, GTP, TTP, UTP, CTP, dATP, dGTP, dTTP, dUTP, dCTP, synthetic analogs), precursors for each nucleotide, non-naturally occurring nucleotides and their precursors or any other molecule that can be incorporated into a growing polymer chain by a given polymerase.

As used herein, a "nucleic acid" shall mean any nucleic acid molecule, including, without limitation, DNA, RNA, and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of a reverse transcriptase. It is well known that DNA (deoxyribonucleic acid) is a chain of nucleotides consisting of 4 types of nucleotides—A (adenine), T (thymine), C (cytosine), and G (guanine)—and that RNA (ribonucleic acid) is a chain of nucleotides consisting of 4 types of nucleotides—A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)), and cytosine (C) pairs with guanine (G), so that each of these base pairs forms a double strand. As used herein, "nucleic acid sequencing data", "nucleic acid sequencing information", "nucleic acid sequence", "genomic sequence", "genetic sequence", "fragment sequence", or "nucleic acid sequencing read" denotes any information or data that is indicative of the order of the nucleotide bases (e.g., adenine, guanine, cytosine, and thymine/uracil) in a molecule (e.g., a whole genome, a whole transcriptome, an exome, oligonucleotide, polynucleotide, fragment, etc.) of DNA or RNA.

Reference to a base, a nucleotide, or to another molecule may be in the singular or plural. That is, "a base" may refer to a single molecule of that base or to a plurality of the base, e.g., in a solution.

As used herein, the phrase "a clonal plurality of nucleic acids" or "a clonal population of nucleic acids" or "a cluster" or "a polony" refers to a set of nucleic acid products that are substantially or completely or essentially identical to each other, and they are complementary copies of the template nucleic acid strand from which they are synthesized.

As used herein, a "polynucleotide", also called a nucleic acid, is a covalently linked series of nucleotides in which the 3' position of the pentose of one nucleotide is joined by a phosphodiester group to the 5' position of the next. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound having a linear backbone of nucleotides. Oligonucleotides, also termed oligomers, are generally shorter chained polynucleotides.

As used herein, "complementary" generally refers to specific nucleotide duplexing to form canonical Watson-Crick base pairs, as is understood by those skilled in the art. However, complementary also includes base-pairing of nucleotide analogs that are capable of universal base-pairing with A, T, G or C nucleotides and locked nucleic acids that enhance the thermal stability of duplexes. One skilled in the art will recognize that hybridization stringency is a determinant in the degree of match or mismatch in the duplex formed by hybridization.

As used herein, "moiety" refers to one of two or more parts into which something may be divided, such as, for example, the various parts of a tether, a molecule or a probe.

A "polymerase" is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), Bst DNA Polymerase Large Fragment, Stoeffel Fragment, 9° N DNA Polymerase, Pfu DNA Polymerase, Tfl DNA Polymerase, RepliPHI Phi29 Polymerase, Tli DNA polymerase, eukaryotic DNA polymerase beta, telomerase, Therminator polymerase (New England Biolabs), KOD HiFi. DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in U.S. Pat. Appl. Pub. No. 2007/0048748 and in U.S. Pat. Nos. 6,329,178; 6,602,695; and 6,395,524. These polymerases include wild-type, mutant isoforms, and genetically engineered variants such as exo-polymerases and other mutants, e.g., that tolerate labeled nucleotides and incorporate them into a strand of nucleic acid.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

Embodiments of the Technology

The technology relates generally to methods, compositions, systems, and kits for DNA sequencing using a sequencing-by-synthesis approach. Although the disclosure herein refers to certain illustrated embodiments, it is to be understood that these embodiments are presented by way of example and not by way of limitation.

Methods

Some embodiments of the technology provide for methods of DNA sequencing-by-synthesis in which differences in signal amplitude, rather than differences in signal wavelength, identify bases incorporated during, for example, a sequencing-by-synthesis reaction. In some embodiments, an ensemble based (e.g., a polymerase colony ("polony") or clonal colony) sequencing approach is used. These approaches sequence multiple identical or substantially identical copies of a DNA molecule that form a cluster of template molecules. Methods of forming clusters are provided, e.g., in U.S. Pat. No. 7,115,400. In some embodiments, the clusters are immobilized on a solid support such as a bead. These clusters typically result from amplifying a single originating DNA molecule; thus, each cluster represents the single molecule that initiated the amplification. For example, in the "bridge amplification" process used in Solexa sequencing, approximately 1 million copies of the original DNA molecule fragment are present in such a cluster. Then, depending on the sequencing chemistry and methodology of particular embodiments, bases are added to the collection of clusters (or, equivalently, colonies, polonies). In an ensemble method according to the present technology, the extent of labeling is directly associated with the intensity of the signal produced. For example, a base having a labeled fraction of 0.25 will produce a signal approximately 25% of the signal for a base having a labeled fraction of 1.00.

In general, two approaches for base addition are used in ensemble-based sequencing-by-synthesis: in the first, the bases are provided one at a time; in the second, bases are modified with identifying moieties so that the base type of the incorporated nucleotide is identified as synthesis proceeds. In some embodiments, synthesis is synchronously controlled by adding one base at a time (see, e.g., Margulies, M. et al. "Genome sequencing in microfabricated high-density picolitre reactors", *Nature* 437: 376-380 (2005); Harris, T. D. et al. "Single-molecule DNA sequencing of a viral genome", *Science* 320: 106-109 (2008)) or by using nucleotides that are reversibly blocked. In particular embodiments, extension is momentarily blocked following each base addition by using modified nucleotides (e.g., nucleotide reversible terminators as described in, e.g., WO2004/018497; U.S. Pat. Appl. Pub. No. 2007/0166705; Bentley, D. R. et al. "Accurate whole human genome sequencing using reversible terminator chemistry", *Nature* 456: 53-59 (2008); Turcatti, G. et al. "A new class of cleavable fluorescent nucleotides: synthesis and optimization as reversible terminators for DNA sequencing by synthesis", *Nucleic Acids Res.* 36: e25 (2008); Guo, J. et al. "Four-color DNA sequencing with 3'-O-modified nucleotide reversible terminators and chemically cleavable fluorescent dideoxynucleotides", *Proc. Natl. Acad. Sci. USA* 105: 9145-9150 (2008); Ju, J. et al. "Four-color DNA sequencing by synthesis using cleavable fluorescent nucleotide reversible terminators", *Proc. Natl. Acad. Sci. USA* 103: 19635-19640 (2006); Seo, T. S. et al. "Four-color DNA sequencing by synthesis on a chip using photocleavable fluorescent nucleotides", *Proc. Natl. Acad. Sci. USA* 102: 5926-5931 (2005); Wu, W. et al. "Termination of DNA synthesis by N6-alkylated, not 3'-O-alkylated, photocleavable 2'-deoxyadenosine triphosphates", *Nucleic Acids Res.* 35: 6339-6349 (2007)) or by omitting reaction components such as divalent metal ions (see, e.g., WO 2005/123957; U.S. Pat. Appl. Pub. No. 20060051807).

Typically, each base addition is followed by a washing step to remove excess reactants. Then, while synthesis is stopped, clusters are imaged to determine which base was added. In embodiments when one base is added per reaction cycle, the successful incorporation of a base indicates the base (and thus the sequence) at that position. These base additions are detected typically by fluorescence (see, e.g., Harris, supra) or by enzyme cascades that identify the release of pyrophosphate by the production of light (see, e.g., Margulies, supra; Bentley, supra). According to the technology provided herein, base identity is associated with the intensity of the signal generated, which, in turn, is associated with the extent of labeling of the bases (and, in some embodiments, to the extent of labeling and the color).

When all bases are added simultaneously, bases are conventionally discriminated by different tags (e.g., fluorescent moieties) attached to each base (see, e.g., Korlach, J. et al. "Selective aluminum passivation for targeted immobilization of single DNA polymerase molecules in zero-mode waveguide nanostructures", *Proc. Natl. Acad. Sci. USA* 105: 1176-1181 (2008); U.S. Pat. Appl. Pub. No. US 20030194740; U.S. Pat. Appl. Pub. No. U.S. Pat. Appl. Pub. No. US 20030064366; Turcatti, G., et al. "A new class of cleavable fluorescent nucleotides: synthesis and optimization as reversible terminators for DNA sequencing by synthesis", *Nucleic Acids Res.* 36: e25 (2008); Guo, J. et al. "Four-color DNA sequencing with 3'-O-modified nucleotide reversible terminators and chemically cleavable fluorescent dideoxynucleotides", *Proc. Natl. Acad. Sci. USA* 105: 9145-9150 (2008); Ju, J. et al. "Four-color DNA sequencing by synthesis using cleavable fluorescent nucleotide reversible terminators", *Proc. Natl. Acad. Sci. USA* 103: 19635-19640 (2006); Seo, T. S. et al. "Four-color DNA sequencing by synthesis on a chip using photocleavable fluorescent nucleotides", *Proc. Natl. Acad. Sci. USA* 102: 5926-5931 (2005); Wu, W. et al. "Termination of DNA synthesis by N6-alkylated, not 3'-O-alkylated, photocleavable 2'-deoxyadenosine triphosphates", *Nucleic Acids Res.* 35: 6339-6349 (2007); WO 2006/084132). According to the technology provided herein, base identity is associated with the intensity (e.g., the amplitude) of the signal generated, which, in turn, is associated with the extent of labeling of the bases (and, in some embodiments, to the extent of labeling and the color).

For example, in some embodiments all four nucleotides are added simultaneously to the reaction comprising DNA polymerase and the clusters of template-primer complexes. In some embodiments, the nucleotides carry a fluorescent label and the 3' hydroxyl group is chemically blocked (e.g., with a labeled reversible terminator) so that synthesis stops after a base is incorporated into the growing (synthesized) DNA strand. An imaging step follows each base incorporation step, during which the clusters are imaged. To image the clusters, in some embodiments the fluorescent labels are excited by a laser and then the fluorescence emitted from the clusters is recorded. In some embodiments, the imaging records the color and/or the intensity of the fluorescence. According to embodiments of the present technology, at least two bases are labeled to different extents and thus differences in intensity distinguish the bases from one another. Then, before initiating the next synthetic cycle, the 3' terminal blocking groups are removed to provide a substrate for the incorporation of the next base. The cycles are repeated in this fashion to determine the sequence of the templates one base at a time.

In some embodiments each nucleotide is added one at a time to a reaction mixture containing the nucleic acid target-primer complex and the polymerase, monitoring the reaction for a signal, and removing the base from the reaction. For example, an illustrative embodiment of the method comprises:

1. providing a sequencing primer, a template, a polymerase, and solutions of the four bases A, C, G, and T
2. hybridizing the primer to the template under appropriate chemical and physical conditions
3. adding an aliquot of a solution comprising the A base to the reaction
4. monitoring the reaction for the production of a signal
5. removing the A base from the solution
6. adding an aliquot of a solution comprising the C base to the reaction
7. monitoring the reaction for the production of a signal 8. removing the C base from the solution
9. adding an aliquot of a solution comprising the G base to the reaction
10. monitoring the reaction for the production of a signal
11. removing the G base from the solution
12. adding an aliquot of a solution comprising the T base to the reaction
13. monitoring the reaction for the production of a signal
14. removing the T base from the solution
15. repeating steps 3-14 until the template is sequenced.

During each monitoring step, the detection of an output signal appropriate for the base added in the previous step indicates a successful incorporation of that base and thus identifies the base incorporated at that step.

Detection may be by conventional modes. For example, if the label is a fluorescent moiety, then detection of an incorporated base may be carried out by using a confocal scanning microscope to scan the collection of clusters (e.g., attached to a surface) with a laser to image a fluorophore bound directly to the incorporated base. Alternatively, a sensitive 2-D detector, such as a charge coupled detector (CCD), can be used to visualize the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g. 10 nm to 10 fm. For a description of scanning near-field optical microscopy, see Moyer et al., *Laser Focus World* (1993) 29:10. Suitable apparatuses used for imaging polynucleotide arrays are known and the technical set-up will be apparent to the skilled person. The detection is preferably used in combination with an analysis system to determine the number and nature of the nucleotides incorporated for each step of synthesis. This analysis, which may be carried out immediately after each synthesis step, or later using recorded data, allows the sequence of the nucleic acid template within a given colony to be determined.

While this exemplary embodiment indicates adding the bases in the order A, C, G, and T, the technology is not limited to this order. Indeed, in some embodiments the bases are added in any permuted order of the set {A C G T} or {A C G U}, e.g., A, G, C, T; A, T, C, G; T, C, G, A, etc. In addition, some embodiments provide that base analogues, modified bases, and other molecules are added instead of A, C, G, and T. It is to be understood that the nucleotides comprising uridine ("U") can be used in place of T and vice-versa. If the sequence being determined is unknown, the nucleotides added are usually applied in a chosen order that is then repeated throughout the analysis, for example as discussed above. If, however, the sequence being determined is known and is being re-sequenced, for example, to determine if small differences are present in the sequence relative to the known sequence, the sequencing determination process may be made quicker by adding the nucleotides at each step in the appropriate order, chosen according to the known sequence. Differences from the given sequence are thus detected by the lack of incorporation of certain nucleotides at particular stages of primer extension.

As an improved method of detecting base addition in SBS, the technology is generally applicable to SBS methods in which bases are differentially labeled to identify them. However, while conventional technologies differentiate bases by color only, the technology provided herein differentiates bases by differences in intensity. In some embodiments, differences in intensity and color differentiate the bases. For example, in some embodiments all four bases are labeled to a different extent. In some embodiments, two colors and two intensities are used in combination to differentiate the bases—e.g., two bases are labeled with a first fluorescent tag to two different extents and the two other bases are labeled with a second fluorescent tag to two different extents. Discussions of tagging and identification schemes are discussed more fully below.

With respect to sequencing-by-synthesis methods and schemes that find use, e.g., as appropriately adapted to the methods provided herein, Morozova and Marra provide a review of some such technologies in *Genomics* 92: 255 (2008); additional discussions are found in Mardis, *Annu. Rev. Genomics Hum. Genet.* (2008) 9:387-402 and in Fuller, et al. (2009) *Nat. Biotechnol.* 27: 1013.

More specifically, some embodiments provide for the use of bases labeled to different extents in an ensemble sequencing-by-synthesis technique such as the following: parallel sequencing of partitioned amplicons (PCT Publication No: WO2006084132); parallel oligonucleotide extension (See, e.g., U.S. Pat. Nos. 5,750,341; 6,306,597); polony sequencing (Mitra et al. (2003) *Analytical Biochemistry* 320: 55-65; Shendure et al. (2005) *Science* 309: 1728-1732; U.S. Pat. Nos. 6,432,360, 6,485,944, 6,511,803); the Solexa single base addition technology (see, e.g., Bennett et al. (2005), *Pharmacogenomics* 6: 373-382; U.S. Pat. Nos. 6,787,308; 6,833,246; herein incorporated by reference in their entireties), the Lynx massively parallel signature sequencing technology (Brenner et al. (2000). *Nat. Biotechnol.* 18: 630-634; U.S. Pat. Nos. 5,695,934; 5,714,330), and the Adessi PCR colony technology (Adessi et al. (2000). *Nucleic Acid Res.* 28: E87; WO 00018957).

In an exemplary embodiment, Solexa sequencing is used. In the Solexa/Illumina platform (Voelkerding et al., *Clinical Chem.*, 55:641-658, 2009; MacLean et al., *Nature Rev. Microbial.* 7: 287-296; U.S. Pat. Nos. 6,833,246; 7,115,400; 6,969,488; and 6,787,308, each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure (and after several rounds of amplification, a cluster) on the surface of the flow cell. These loops of DNA are denatured and cleaved. Forward strands are then sequenced with reversible dye terminators. The sequence of incorporated nucleotides is determined by detection of post-incorporation fluorescence (e.g., by differences in intensity), with each fluor and block removed prior to the next cycle of dNTP addition. Sequence read length ranges from 36 nucleotides to over 50 nucleotides, with overall output exceeding 1 billion nucleotide pairs per analytical run.

In some embodiments, a calibration sequence is used to differentiate the signal intensities associated with the bases. For example, such a calibration sequence comprises, in some embodiments, each of the four bases in a known order so that a sequencing instrument is calibrated to recognize the signal intensities (due to the label fraction) expected for each of the bases complementary to the calibration sequence. In some embodiments the calibration sequence is attached to the beginning of each target nucleic acid to be sequenced. In some embodiments, the calibration sequence is not attached to the target sequence but is used to calibrate the sequencing instrument before acquiring the sequence of the target nucleic acid. In some embodiments, the calibration is used for more than one sequencing run. For embodiments in which a combination of colors and extents of labeling (and consequent signal intensities) differentiates bases from one another, the calibration sequence is adjusted appropriately. The calibration sequence is any length that provides adequate calibration. In some embodiments the calibration sequence is four bases long; in some embodiments the calibration sequence is 5, 6, 7, 8, 9, 10, 16, 20, 24, 28, 32, 64, or more bases long.

Some embodiments provide methods for the detection of molecules or differential labeling of samples using detection reagents labeled to different extents. Differences in intensity identify the molecules and differentiate the molecules from each other. For example, some methods comprise contacting a sample (e.g., a cell, tissue, fluid, etc.) with two or more antibodies wherein each antibody is labeled to a different extent; some methods comprise contacting a sample (e.g., a cell, tissue, fluid, etc.) with two or more labeled oligonucleotide probes wherein each probe is labeled to a different extent. In some embodiments the same label (e.g., a tag or fluorescent moiety) is linked to the detection reagents and in some embodiments, combinations of color and labeled fraction are used to identify and differentiate the detection reagents. The methods comprise differentiating two or more molecules, samples, tissues, cells, etc. from each other by associating a difference in intensity (and, in some embodiments also differences in color) with a detection reagent.

Compositions

The technology provides compositions, e.g., compositions of nucleotide bases alone or in combination wherein the extent of labeling differs for at least two of the bases. As noted above, the signal intensity produced and detected during the SBS reaction varies proportionally with the labeled fraction of each base. For example, reducing the extent of labeling reduces the signal intensity and increasing the extent of labeling increases the signal intensity.

In some embodiments, the extent of labeling (or "labeled fraction") differs among the four bases, allowing for differentiating each base from the three others, e.g., as each base is incorporated in an ensemble SBS reaction and a signal is produced. As used herein, the "extent of labeling" or "labeled fraction" refers to the fraction or portion of base molecules of one type that is labeled. The extent of labeling or the labeled fraction may be a fraction from 0.00 to 1.00 (alternatively, a percentage from 0% to 100%). For instance, if the number of individual A base molecules (e.g., in a solution) is 100 and the number of individual A base molecules that are labeled is 25, then the extent of labeling for A is 0.25 or 25%. In this exemplary embodiment, the extent of labeling for the other three bases C, G, and T, is 0.50 (50%), 0.75 (75%), and 1.00 (100%), respectively. Various embodiments provide extents of labeling other than these exemplary values. Indeed, any combination of labeled fractions is contemplated by the technology provided that the four bases can be distinguished from one another based on the differences in the extents of labeling and the subsequent signals produced in a SBS reaction. In various embodiments, any of the four bases is labeled at an extent of labeling that is 10%, 20%, 30%, 40%, 50%, 60%, 70%, 80, 90%, and/or 100%, and intermediate values between these listed values, provided the labeled fraction for the bases is sufficient to differentiate the bases from one another.

In some embodiments, a first value representing the labeled fraction for one base and a second value representing the labeled fraction for a second base are chosen so that low multiples of the two values are rarely the same (e.g., generally, when multiplied by a number less than 20). Such a scheme finds use in differentiating homopolymeric runs of single bases from one another and from single bases, e.g., in some sequencing schemes where the presence of the same base in consecutive positions produces a stronger signal than a signal produced by one base.

In some embodiments, bases are differentiated by both color and labeled fraction. For example, in some embodiments two bases are labeled with the same fluorescent tag at two different fractions and the other two bases are labeled with a different fluorescent tag at two different fractions, which may be the same or different fractions than the fractions used for the first two bases. This approach is extended to include embodiments in which three bases are labeled with the same fluorescent tag at three different fractions and the fourth base is labeled with a different fluorescent tag and to include embodiments in which three bases are labeled using three different fluorescent tags and the fourth base is labeled using one of the same fluorescent tags as is used for the first three bases, but at a different extent of labeling. Some embodiments contemplate the use of four different tags (e.g., fluorescent moieties) and four different label fractions, e.g., to provide a redundant identification scheme.

Compositions provided by the present technology include solutions of four bases wherein at least two bases are labeled to a different extent. Embodiments of compositions generally comprise a buffer known in the art and optionally comprise other salts and preservatives known to those in the art, e.g., to maintain the stability of the composition. Various embodiments include compositions comprising one base or mixtures of 2, 3, 4, or more bases. The bases in these compositions are labeled to different extents and/or with different fluorescent tags using identification schemes as discussed above.

Some embodiments provide a composition comprising a calibration oligonucleotide comprising or consisting of a known sequence of bases. In some embodiments, the calibration oligonucleotide comprises or consists of 4, 5, 6, 7, 8 or more bases whose sequence is known. The oligonucleotide is, in some embodiments, synthesized chemically.

According to the technology, the bases are labeled with a moiety that results in the production of a detectable signal upon the incorporation of the base into the DNA strand being synthesized. In some embodiments, the moiety produces a signal (e.g., fluorescence) prior to incorporation and/or after incorporation. In some embodiments, the moiety is linked in such a way that is appropriate for removing the moiety after incorporation or after imaging. The labeling moiety is, in some embodiments, a fluorescent organic dye derivatized for attachment to the base directly or via a linker. Practical guidance is available in the literature that provides a list of fluorescent and chromogenic molecules and their relevant optical properties (see, for example, Berlman, *Handbook of Fluorescence Spectra of Aromatic Molecules,* 2nd Edition (Academic Press, New York, 1971); Griffiths, *Colour and Constitution of Organic Molecules* (Academic Press, New York, 1976); Bishop, Ed., *Indicators* (Pergamon Press, Oxford, 1972); Haugland, *Handbook of Fluorescent Probes and Research Chemicals* (Molecular Probes, Eugene, 1992) Pringsheim, Fluorescence and Phosphorescence (Interscience Publishers, New York, 1949); and the like.

Further, there is guidance in the literature for derivatizing fluorophore molecules for covalent attachment via common reactive groups that can be added to a nucleotide, as exemplified by Haugland (supra); Ullman et al, U.S. Pat. No. 3,996,345; Khanna et al, U.S. Pat. No. 4,351,760. There are many linking moieties and methodologies for attaching fluorescent or quencher moieties to nucleotides, as exemplified by the following references: Eckstein, editor, *Oligonucleotides and Analogues: A Practical Approach* (IRL Press, Oxford, 1991); Zuckerman et al. (1987), *Nucleic Acids Research* 15: 5305-5321; Sharma et al. (1991), *Nucleic Acids Research* 19: 3019; Giusti et al., *PCR Methods and Applications* 2: 223-227 (1993); Fung et al., U.S. Pat. No. 4,757,141; Stabinsky, U.S. Pat. No. 4,739,044; Agrawal et al. (1990), *Tetrahedron Letters* 31: 1543-1546; Sproat et al. (1987), *Nucleic Acids Research* 15: 4837; Nelson et al. (1989), *Nucleic Acids Research* 17: 7187-7194; and the like. A number of DNA fluorescence-based sequencing methodologies are described, e.g., in Birren et al., *Genome Analysis: Analyzing DNA*, (Cold Spring Harbor, N.Y.).

Embodiments of the technology comprise compositions comprising a target nucleic acid template. In some embodiments, the composition comprises a primer, e.g., in some embodiments that is bound to the target nucleic acid template.

The target nucleic acid is not critical and can come from a variety of standard sources. It can be mRNA, ribosomal RNA, genomic DNA, or cDNA. When the target is from a biological source, procedures are known for extracting nucleic acid and optionally amplifying it to a concentration convenient for genotyping or sequence work. Nucleic acid can be obtained from any living cell of a person, animal, or plant (and in many cases from dead cells or any other matter of biological origin). Humans, pathogenic microbes, and viruses are particularly interesting sources. Nucleic acid amplification methods are also known. Preferably, the amplification is carried out by polymerase chain reaction (PCR) (U.S. Pat. Nos. 4,683,202; 4,683,195; and 4,889,818; Gyllenstein et al (1988) *Proc. Natl. Acad. Sci. USA* 85: 7652-7656; Ochman et al. (1988) *Genetics* 120: 621-623; Loh et al (1989) *Science* 243: 217-220; Innis et al (1990) *PCR Protocols* (Academic Press, San Diego, Calif.). Other amplification methods known in the art can be used, including but not limited to ligase chain reaction (see, e.g., EP 320308), use of Q-beta replicase, or methods listed in Kricka et al., 1995, *Molecular Probing, Blotting, and Sequencing*, Chap. 1 and Table IX (Academic Press, New York).

The technology provided herein relates to the use of a polymerase in a sequencing reaction. In general, the polymerases that find use in the technology tolerate labels in various positions, e.g., on the nucleobase, on the gamma-phosphate, on the 3' hydroxyl. For instance, polymerases that find use in the technology are T7 DNA polymerase, T5 DNA polymerase, HIV reverse transcriptase, *E. coli* DNA pol I, T4 DNA polymerase, T7 RNA polymerase, Taq DNA polymerase and *E. coli* RNA polymerase. In some embodiments, an exonuclease-defective polymerases is used. In some embodiments (e.g., a reversible terminator technology), a polymerase having an exonuclease activity is used for some or all steps.

The primers (e.g., as used for syntheses by DNA polymerase) or promoters (e.g., as used for syntheses by RNA polymerase) are typically synthetically made using conventional nucleic acid synthesis technology, e.g., using an automated DNA synthesizer and standard chemistries, such as phosphoramidite chemistry, e.g., as disclosed in the following references: Beaucage and Iyer, *Tetrahedron* 48: 2223-211 (1992); U.S. Pat. Nos. 4,980,460; 4,725,677; 4,415,732; 4,458,066; and 4,973,679; and the like. Alternative chemistries, e.g., resulting in non-natural backbone groups, such as phosphorothioate, phosphoramidate, and the like, may also be employed provided that the resulting oligonucleotides are compatible with the polymerase. They can be ordered commercially from a variety of companies that specialize in custom oligonucleotides such as Operon, IDT, Dharmacon, etc.

Primers in combination with polymerases are used to sequence target DNA. Primer length is selected to provide for hybridization to complementary template DNA. The primers will generally be at least 10 nt in length, usually at least between 15 and 30 nt in length. Primers are designed to hybridize to known internal sites on the subject target DNA. Alternatively, the primers can bind to synthetic oligonucleotide adaptors joined to the ends of target DNA by a ligase. Similarly, where promoters are used, they can be internal to the target DNA or ligated as adaptors to the ends.

The reaction mixture for the sequencing comprises an aqueous buffer medium that is optimized for the particular polymerase chosen. In general, the buffer includes a source of monovalent ions, a source of divalent cations, and a buffering agent. Any convenient source of monovalent ions, such as potassium chloride, potassium acetate, potassium acetate, potassium glutamate, ammonium chloride, ammonium sulfate, and the like may be employed.

The divalent cation may be magnesium, managanese, zinc, and the like, where the cation will typically be magnesium. Any convenient source of magnesium cation may be employed, including $MgCl_2$, magnesium acetate, and the like. The amount of Mg ion present in the buffer may range from 0.5 to 20 mM, but will preferably range from about 1 to 12 mM, more preferably from 2 to 10 mM, and will ideally be about 5 mM.

Representative buffering agents or salts that may be present in compositions according to the technology described (e.g., in a composition comprising a labeled nucleotide or in a SBS reaction) include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5. Other agents which may be present in the buffer medium include chelating agents, such as EDTA, EGTA and the like.

Some embodiments provide compositions for the detection of molecules or for the differential labeling of samples using detection reagents labeled to different extents. Differences in intensity identify the molecules and differentiate the molecules from each other. For example, some compositions comprise two or more antibodies wherein each antibody is labeled to a different extent; some compositions comprise two or more labeled oligonucleotide probes wherein each probe is labeled to a different extent. In some embodiments the same label (e.g., a tag or fluorescent moiety) is linked to the detection reagents and in some embodiments, combinations of color and labeled fraction are used to identify and differentiate the detection reagents. In some embodiments, one or more of the labeled detection reagents is/are one of the following: an aptamer, a protein nucleic acid, a locked nucleic acid, an RNA, a DNA, an antibody fragment, a small molecule, a protein, a DNA binding domain of a protein, a protein binding domain of a protein, and other detection reagents known in the art.

Data Analysis

Some embodiments comprise a computer system upon which embodiments of the present teachings may be implemented. In various embodiments, a computer system includes a bus or other communication mechanism for communicating information, and a processor coupled with the bus for processing information. In various embodiments, the computer system includes a memory, which can be a random access memory (RAM) or other dynamic storage device, coupled to the bus for identifying bases (e.g., making "base calls"), and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user. An input device, including alphanumeric and other keys, can be coupled to the bus for communicating information and command selections to the processor. Another type of user input device is a cursor control, such as a mouse, a trackball, or cursor direction keys for communicating direction information and command selections to the processor and for controlling cursor movement on the display. This input device typically has two degrees of freedom in two axes, a first axis (e.g., x) and a second axis (e.g., y), that allows the device to specify positions in a plane.

A computer system can perform embodiments of the present technology. Consistent with certain implementations of the present teachings, results can be provided by the computer system in response to the processor executing one or more sequences of one or more instructions contained in the memory. Such instructions can be read into the memory from another computer-readable medium, such as a storage device. Execution of the sequences of instructions contained in the memory can cause the processor to perform the methods described herein. Alternatively, hard-wired circuitry can be used in place of or in combination with software instructions to implement the present teachings. Thus, implementations of the present teachings are not limited to any specific combination of hardware circuitry and software.

The term "computer-readable medium" as used herein refers to any media that participates in providing instructions to the processor for execution. Such a medium can take many forms, including but not limited to, non-volatile media, volatile media, and transmission media. Examples of non-volatile media can include, but are not limited to, optical or magnetic disks, such as a storage device. Examples of volatile media can include, but are not limited to, dynamic memory. Examples of transmission media can include, but are not limited to, coaxial cables, copper wire, and fiber optics, including the wires that comprise the bus.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to the processor for execution. For example, the instructions can initially be carried on the magnetic disk of a remote computer. The remote computer can load the instructions into its dynamic memory and send the instructions over a network connection (e.g., a LAN, a WAN, the internet, a telephone line). A local computer system can receive the data and transmit it to the bus. The bus can carry the data to the memory, from which the processor retrieves and executes the instructions. The instructions received by the memory may optionally be stored on a storage device either before or after execution by the processor.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with such a computer system, some embodiments of the technology provided herein further comprise functionalities for collecting, storing, and/or analyzing data (e.g., nucleotide sequence data). For example, some embodiments contemplate a system that comprises a processor, a memory, and/or a database for, e.g., storing and executing instructions, analyzing imaging data from a SBS reaction, performing calculations using the data, transforming the data, and storing the data. It some embodiments, a base-calling algorithm assigns a sequence of bases to the data and associates quality scores to base calls based on a statistical model. In some embodiments, the system is configured to assemble a sequence from multiple sub-sequences, in some instances accounting for overlap and calculating a consensus sequence. In some embodiments, a sequence determined from a SBS reaction is aligned to a reference sequence or to a scaffold.

Many diagnostics involve determining the presence of, or a nucleotide sequence of, one or more nucleic acids. Thus, in some embodiments, an equation comprising variables representing the presence or sequence properties of multiple nucleic acids produces a value that finds use in making a diagnosis or assessing the presence or qualities of a nucleic acid. As such, in some embodiments this value is presented by a device, e.g., by an indicator related to the result (e.g., an LED, an icon on an LCD, a sound, or the like). In some embodiments, a device stores the value, transmits the value, or uses the value for additional calculations.

Moreover, in some embodiments a processor is configured to control the sequencing reactions and collect the data (e.g., images). In some embodiments, the processor is used to initiate and/or terminate each round of sequencing and data collection relating to a sequencing reaction. Some embodiments comprise a processor configured to analyze the dataset of intensities and/or colors acquired during the SBS reaction and discern the sequence of the target nucleic acid and/or of its complement.

In some embodiments, a device that comprises a user interface (e.g., a keyboard, buttons, dials, switches, and the like) for receiving user input is used by the processor to direct a measurement. In some embodiments, the device further comprises a data output for transmitting (e.g., by a wired or wireless connection) data to an external destination, e.g., a computer, a display, a network, and/or an external storage medium.

In some embodiments, the technology finds use in assaying the presence of one or more nucleic acids and/or providing the sequence of one or more nucleic acids. Accordingly, the technology provided herein finds use in the medical, clinical, and emergency medical fields. In some embodiments a device is used to assay biological samples. In such an assay, the biological sample comprises a nucleic acid and sequencing the nucleic acid is indicative of a state or a property of the sample and, in some embodiments, the subject from which the sample was taken. Some relevant samples include, but are not limited to, whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate, a tissue homogenate, a cell homogenate, or the like.

The sequence of output signals provides the sequence of the synthesized DNA and, by the rules of base complementarity, also thus provides the sequence of the template strand.

Apparatuses

A further aspect of the invention provides an apparatus for carrying out the methods or for preparing the compositions of the technology. Such apparatus might comprise, for example, a plurality of nucleic acid templates and primers bound, preferably covalently, to a solid support, together with a nucleic acid polymerase, a plurality of nucleotides such as those described above, a proportion of which are labeled (the labeled fraction), and a functionality for controlling temperature and/or nucleotide additions. Preferably the apparatus also comprises a detecting functionality for detecting and distinguishing signals from individual nucleic acid clusters. Such a detecting functionality might comprise a charge-coupled device operatively connected to a magnifying device such as a microscope. Preferably any apparatuses of the invention are provided in an automated form, e.g., under the control of a program of steps and decisions, e.g., as implemented in computer software.

Some embodiments of such an apparatus include a fluidic delivery and control unit, a sample processing unit, a signal detection unit, and a data acquisition, analysis and control unit. Various embodiments of the apparatus can provide for automated sequencing that can be used to gather sequence information from a plurality of sequences in parallel, e.g., substantially simultaneously.

In various embodiments, the fluidics delivery and control unit includes a reagent delivery system. The reagent delivery system can include a reagent reservoir for the storage of various reagents (e.g., compositions of nucleotides according to the technology). The reagents can include RNA-based primers, forward/reverse DNA primers, oligonucleotide mixtures for ligation sequencing, nucleotide mixtures for sequencing-by-synthesis, buffers, wash reagents, blocking reagent, stripping reagents, and the like. Additionally, the reagent delivery system can include a pipetting system or a continuous flow system that connects the sample processing unit with the reagent reservoir.

In various embodiments, the sample processing unit can include a sample chamber, such as flow cell, a substrate, a micro-array, a multi-well tray, or the like. The sample processing unit can include multiple lanes, multiple channels, multiple wells, or other modes of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit can include an imaging or detection sensor. The signal detection unit can include an excitation system to cause a probe, such as a fluorescent dye, to emit a signal. The excitation system can include an illumination source, such as arc lamp, a laser, a light emitting diode (LED), or the like. In particular embodiments, the signal detection unit can include optics for the transmission of light from an illumination source to the sample or from the sample to the imaging or detection sensor. Alternatively, the signal detection unit may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal.

In various embodiments, data acquisition analysis and control unit can monitor various system parameters. The system parameters can include the temperature of various portions of the instrument, such as the sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of such an instrument can be used to practice a variety of sequencing methods including ligation-based methods, sequencing by synthesis, single molecule methods, and other sequencing techniques. Ligation sequencing can include single ligation techniques, or change ligation techniques where multiple ligations are performed in sequence on a single primary. Sequencing by synthesis can include the incorporation of dye labeled nucleotides, chain termination, or the like. Single molecule techniques can include staggered sequencing, where the sequencing reactions are paused to determine the identity of the incorporated nucleotide.

In various embodiments, the sequencing instrument can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument can obtain the sequence information from a single nucleic acid molecule or from a group of substantially identical nucleic acid molecules.

In various embodiments, the sequencing instrument can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Some embodiments comprise a system for reconstructing a nucleic acid sequence in accordance with the various embodiments provided herein. The system can include a nucleic acid sequencer, a sample sequence data storage, a reference sequence data storage, and an analytics computing device/server/node. In various embodiments, the analytics computing device/server/node can be a workstation, a mainframe computer, a personal computer, a mobile device, etc.

The nucleic acid sequencer can be configured to analyze (e.g., interrogate) a nucleic acid fragment (e.g., single fragment, mate-pair fragment, paired-end fragment, etc.) utilizing all available varieties of techniques, platforms, or technologies to obtain nucleic acid sequence information, e.g., using an ensemble sequencing by synthesis. In various embodiments, the nucleic acid sequencer can be in communications with the sample sequence data storage either directly via a data cable (e.g., a serial cable, a direct cable connection, etc.) or bus linkage or, alternatively, through a network connection (e.g., Internet, LAN, WAN, VPN, etc.). In various embodiments, the network connection can be a "hardwired" physical connection. For example, the nucleic acid sequencer can be communicatively connected (via Category 5 (CATS), fiber optic, or equivalent cabling) to a data server that can be communicatively connected (via CATS, fiber optic, or equivalent cabling) through the internet and to the sample sequence data storage. In various embodiments, the network connection can be a wireless network connection (e.g., Wi-Fi, WLAN, etc.), for example, utilizing an 802.11b/g or equivalent transmission format. In practice, the network connection utilized is dependent upon the particular requirements of the system. In various embodiments, the sample sequence data storage can be an integrated part of the nucleic acid sequencer.

In various embodiments, the sample sequence data storage can be any database storage device, system, or implementation (e.g., data storage partition, etc.) that is configured to organize and store nucleic acid sequence read data generated by nucleic acid sequencer such that the data can be searched and retrieved manually (e.g., by a database administrator/client operator) or automatically by way of a computer program/application/software script. In various embodiments, the reference data storage can be any database device, storage system, or implementation (e.g., data storage partition, etc.) that is configured to organize and store reference sequences (e.g., whole/partial genome, whole/partial exome, etc.) such that the data can be searched and retrieved manually (e.g., by a database administrator/client operator) or automatically by way of a computer program/application/software script. In various embodiments, the sample nucleic acid sequencing read data can be stored on the sample sequence data storage and/or the reference data storage in a variety of different data file types/formats, including, but not limited to: *.fasta, *.csfasta, *seq.txt, *qseq.txt, *.fastq, *.sff, *prb.txt, *.sms, *srs and/or *.qv.

In various embodiments, the sample sequence data storage and the reference data storage are independent standalone devices/systems or implemented on different devices. In various embodiments, the sample sequence data storage and the reference data storage are implemented on the same device/system. In various embodiments, the sample sequence data storage and/or the reference data storage can be implemented on the analytics computing device/server/node.

The analytics computing device/server/node can be in communications with the sample sequence data storage and the reference data storage either directly via a data cable (e.g., serial cable, direct cable connection, etc.) or bus linkage or, alternatively, through a network connection (e.g., Internet, LAN, WAN, VPN, etc.). In various embodiments, the analytics computing device/server/node can host a reference mapping engine, a de novo mapping module, and/or a tertiary analysis engine. In various embodiments, the reference mapping engine can be configured to obtain sample nucleic acid sequence reads from the sample data storage and map them against one or more reference sequences obtained from the reference data storage to assemble the reads into a sequence that is similar but not necessarily identical to the reference sequence using all varieties of reference mapping/alignment techniques and methods. The reassembled sequence can then be further analyzed by one or more optional tertiary analysis engines to identify differences in the genetic makeup (genotype), gene expression, or epigenetic status of individuals that can result in large differences in physical characteristics (phenotype). For example, in various embodiments, the tertiary analysis engine can be configured to identify various genomic variants (in the assembled sequence) due to mutations, recombination/crossover, or genetic drift. Examples of types of genomic variants include, but are not limited to: single nucleotide polymorphisms (SNPs), copy number variations (CNVs), insertions/deletions (Indels), inversions, etc.

The optional de novo mapping module can be configured to assemble sample nucleic acid sequence reads from the sample data storage into new and previously unknown sequences.

It should be understood, however, that the various engines and modules hosted on the analytics computing device/server/node can be combined or collapsed into a single engine or module, depending on the requirements of the particular application or system architecture. Moreover, in various embodiments, the analytics computing device/server/node can host additional engines or modules as needed by the particular application or system architecture.

In various embodiments, the mapping and/or tertiary analysis engines are configured to process the nucleic acid and/or reference sequence reads in signal amplitude space. In various embodiments, the mapping and/or tertiary analysis engines are configured to process the nucleic acid and/or reference sequence reads in color space. It should be understood, however, that the mapping and/or tertiary analysis engines disclosed herein can process or analyze nucleic acid sequence data in any schema or format as long as the schema or format can convey the base identity and position of the nucleic acid sequence.

In various embodiments, the sample nucleic acid sequencing read and referenced sequence data can be supplied to the analytics computing device/server/node in a variety of different input data file types/formats, including, but not limited to: *.fasta, *.csfasta, *seq.txt, *qseq.txt, *.fastq, *.sff, *prb.txt, *.sms, *srs and/or *.qv.

Uses

The technology provides the use of the methods of the technology, or the compositions of the technology, for sequencing and/or re-sequencing nucleic acid molecules for gene expression monitoring, genetic diversity profiling, diagnosis, screening, whole genome sequencing, whole genome polymorphism discovery and scoring, or any other application involving the analysis of nucleic acids where sequence or partial sequence information is relevant.

Kits

A yet further aspect of the invention provides a kit for use in sequencing, re-sequencing, gene expression monitoring, genetic diversity profiling, diagnosis, screening, whole genome sequencing, whole genome polymorphism discovery and scoring, or any other application involving the sequencing of nucleic acids. In some embodiments, kits comprise at least one nucleotide labeled to a known extent (e.g., having a known labeled fraction) and, optionally, a calibration oligonucleotide comprising a known sequence. In some embodiments, a kit is provided for the detection of molecules using detection reagents labeled to different extents. Differences in intensity identify the molecules and differentiate the molecules from each other. For example, some kits comprise two or more antibodies wherein each antibody is labeled to a different extent; some kits comprise two or more labeled oligonucleotide probes wherein each probe is labeled to a different extent. In some embodiments the same label (e.g., a tag or fluorescent moiety) is linked to the detection reagents and in some embodiments, combinations of color and labeled fraction are used to identify and differentiate the detection reagents.

Moreover, processes and systems for sequencing that may be adapted for use with the technology are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and U.S. Pat. No. 7,170,050, entitled "Apparatus and methods for optical analysis of molecules", issued Jan. 30, 2007 to Turner et al.; and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flowcell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analogue incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in related fields are intended to be within the scope of the following claims.

I claim:

1. A method for sequencing a target nucleic acid, the method comprising:
   a) detecting a first amplitude of a first signal produced from a plurality of a first nucleotide base in a calibration oligonucleotide wherein a first known fraction of said plurality of a first nucleotide base in said calibration oligonucleotide is labeled with a fluorescent label;
   b) detecting a second amplitude of a second signal from a plurality of a second nucleotide base in said calibration oligonucleotide wherein a second known fraction of said plurality of a second nucleotide base is labeled with said fluorescent label, wherein said first known fraction and said second known fraction are different known fractions, wherein said different known fractions differ between a plurality of different nucleotide bases in said calibration oligonucleotide, wherein said first amplitude is detectably different than said second amplitude, and wherein said calibration oligonucleotide comprises each of four different bases in known order;

c) detecting a first amplitude of a first signal produced from a plurality of a first nucleotide base in said target nucleic acid wherein a first known fraction of said plurality of a first nucleotide base is labeled with a fluorescent label;

d) detecting a second amplitude of a second signal from a plurality of a second nucleotide base in said target nucleic acid wherein a second known fraction of said plurality of a second nucleotide base is labeled with said fluorescent label wherein said first known fraction and said second known fraction are different known fractions, wherein said different known fractions differ between a plurality of different nucleotide bases in said target nucleic acid, wherein said first amplitude is detectably different than said second amplitude, and wherein the same nucleotide base in said calibration oligonucleotide and in said target nucleic acid is labeled with the same known fraction of said label;

e) associating said amplitude of said first signal with said first nucleotide base to identify said first nucleotide base in said calibration oligonucleotide and in said target nucleic acid; and f) associating said amplitude of said second signal with said second nucleotide base to identify said second nucleotide base in said calibration oligonucleotide and in said target nucleic acid.

2. The method of claim 1 further comprising providing a first plurality of a first nucleotide base, a second plurality of a second nucleotide base, a third plurality of a third nucleotide base, and a fourth plurality of a fourth nucleotide base, wherein a first fraction of the first plurality of the first base is labeled with a label, a second fraction of the second plurality of the second nucleotide base is labeled with said label, a third fraction of the third plurality of the third nucleotide base is labeled with said label, and a fourth fraction of the fourth plurality of the fourth nucleotide base is labeled with said label.

3. The method of claim 2 wherein the first nucleotide base is A, the second nucleotide base is C, the third nucleotide base is G, and the fourth nucleotide base is T.

4. The method of claim 2 wherein the label is a fluorescent moiety.

5. The method of claim 1 further comprising providing a first plurality of a first nucleotide base, a second plurality of a second nucleotide base, a third plurality of a third nucleotide base, and a fourth plurality of a fourth nucleotide base, wherein a first fraction of the first plurality of the first base is labeled with a first label, a second fraction of the second plurality of the second nucleotide base is labeled with the first label, a third fraction of the third plurality of the third nucleotide base is labeled with a second label, and a fourth fraction of the fourth plurality of the fourth nucleotide base is labeled with the second label.

6. The method of claim 1 further comprising incorporating by polymerization the plurality of the nucleotide base into a plurality of a nucleic acid that is complementary to the target nucleic acid.

7. The method of claim 1 further comprising analyzing a dataset of ordered amplitudes to produce a nucleotide sequence of the target nucleic acid.

* * * * *